United States Patent
Hatakeyama et al.

(10) Patent No.: US 9,162,934 B2
(45) Date of Patent: Oct. 20, 2015

(54) PROCESS FOR PRODUCING OPTICALLY ACTIVE ALCOHOL

(75) Inventors: Taito Hatakeyama, Saitama (JP); Kunihiko Murata, Saitama (JP); Kunihiko Tsutsumi, Saitama (JP); Noriyuki Utsumi, Saitama (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 845 days.

(21) Appl. No.: 13/104,156

(22) Filed: May 10, 2011

(65) Prior Publication Data

US 2011/0282077 A1 Nov. 17, 2011

(30) Foreign Application Priority Data

May 13, 2010 (JP) ................. 2010-111120

(51) Int. Cl.
  *C07C 29/14* (2006.01)
  *C07B 53/00* (2006.01)
  *C07C 29/143* (2006.01)
  *C07C 67/31* (2006.01)
  *C07C 253/30* (2006.01)
  *C07C 29/157* (2006.01)

(52) U.S. Cl.
  CPC ............... *C07B 53/00* (2013.01); *C07C 29/143* (2013.01); *C07C 67/31* (2013.01); *C07C 253/30* (2013.01); *C07B 2200/07* (2013.01); *C07C 29/157* (2013.01)

(58) Field of Classification Search
  CPC ................................................ C07C 29/157
  USPC ............................ 568/881; 549/522; 556/137
  See application file for complete search history.

(56) References Cited

U.S. PATENT DOCUMENTS

| | | | |
|---|---|---|---|
| 6,184,381 B1 | 2/2001 | Ikariya et al. | |
| 6,888,012 B2 * | 5/2005 | Torii et al. | 549/522 |
| 7,601,667 B2 * | 10/2009 | Utsumi et al. | 502/166 |
| 8,232,420 B2 * | 7/2012 | Watanabe et al. | 556/137 |
| 2007/0149831 A1 | 6/2007 | Amano et al. | |
| 2010/0069683 A1 | 3/2010 | Miki et al. | |

FOREIGN PATENT DOCUMENTS

| | | |
|---|---|---|
| CN | 101104614 A | 1/2008 |
| JP | 2962668 | 8/1999 |
| JP | 2005-220041 A | 8/2005 |
| JP | 4090078 | 3/2008 |
| WO | WO 98/42643 | 10/1998 |
| WO | WO 2005/075073 | 8/2005 |
| WO | WO 2005/092830 A1 | 10/2005 |

OTHER PUBLICATIONS

Ohkuma et al, Jol. Amer. Chem. Soc. vol. 126 pp. 8724-8725 (2006).*
Ma, Y. et al., "Asymmetric Transfer Hydrogenation of Prochiral Ketones in Aqueous Media with New Water-Soluble Chiral Vicinal Diamine as Ligand," *Organic Letters* 2003; vol. 5, No. 12: 2103-2106.
Hashiguchi, S. et al., "Asymmetric Transfer Hydrogenation of Aromatic Ketones Catalyzed by Chiral Ruthenium (II) Complexes," *J. Am. Chem. Soc.* 1995; 117:7562-7563.
Fuji, a. et al., "Ruthenium(II)-Catalyzed Asymmetric Transfer Hydrogenation of Ketones Using a Formic Acid-Triethylamine Mixture," *J. Am. Chem. Soc.* 1996; 118:2521-2522.
Wu, X. et al., "Accelerated asymmetric transfer hydrogenation of aromatic ketones in water," *Org. Biomol. Chem.* 2004; 2:1818-1821.
Wu, X. et al., "Asymmetric Transfer Hydrogenation in Water with Platinum Group Metal Catalysts," *Platinum Metals Rev.* 2010; 54(1):3-19.
Wang, C. et al., "Broader, Greener, and More Efficient: Recent Advances in Asymmetric Transfer Hydrogenation," *Chem. Asian J.* 2008; 3:1750-1770.
Zhou, H.-F. et al., "Mixture of poly(ethylene glycol) and water as environmentally friendly media for efficient enantioselective transfer hydrogenation and catalyst recycling," *Journal of Molecular Catalysis A: Chemical* 2007; 275:47-53.
Japanese Office Action issued Jun. 23, 2014, for Application No. 2010-111120.
Notice of Opposition and Statement of the Grounds for Opposition to EP 2394977B dated Oct. 8, 2014, and Communication of a Notice of Opposition dated Oct. 17, 2014 in connection with European Application No. 11003944.3.
Wu et al., Rh III- and Ir III-catalyzed asymmetric transfer hydrogenation of ketones in water. Chemistry. 2008;14(7):2209-22.
Wu et al., A multilateral mechanistic study into asymmetric transfer hydrogenation in water. Chemistry. 2008;14(25):7699-715. doi: 10.1002/chem.200800559.
Extended European Search Report for 11003944.3 mailed Nov. 15, 2011.
Ma, Y. et al., "Asymmetric Transfer Hydrogenation of Prochiral Ketones in Aqueous Media with New Water-Soluble Chiral Vicinal Diamine as Ligand,"*Organic Letters 2003*; vol. 5, No. 12: 2103-2106.

* cited by examiner

*Primary Examiner* — Andrew D Kosar
*Assistant Examiner* — Raymond Covington
(74) *Attorney, Agent, or Firm* — Wolf, Greenfield & Sacks, P.C.

(57) ABSTRACT

The object of the present invention is to solve the problems in the prior arts, and to find more improved reaction conditions for suppressing the racemization of the product and obtaining an optically active alcohol at a high optical purity. The inventors achieved to solve the above problems by using a solvent system that is capable of resolving both an asymmetric catalyst and a formate salt, allowing the hydrogen source and the asymmetric catalyst to be present in the same phase.

11 Claims, No Drawings

PROCESS FOR PRODUCING OPTICALLY ACTIVE ALCOHOL

TECHNICAL FIELD

The invention relates to a process for the production of an optically active alcohol.

BACKGROUND ARTS

Asymmetric ruthenium complexes, rhodium complexes and iridium complexes, which take sulfonyl diamine as a ligand, are useful asymmetric reducing catalysts. These are employed for the asymmetric reduction of a ketone substrate for an efficient production of an optically active alcohol (Patent Literatures 1 and 2).

In Non-patent Literature 1,2-propanol is used as a hydrogen source. This reaction is a reversible equilibrium reaction that gives an optically active alcohol and acetone from ketone substrate and 2-propanol. Therefore, an (S,S) catalyst, for example, reduces acetophenone to give (S)-phenylethanol in a ratio of 99:1 ((S):(R)). However, this reaction preferentially dehydrogenates (S)-phenylethanol in a ratio of 99:1 to give acetophenone, compared to (R)-phenylethanol. Therefore, at initial phase of the reaction, when the concentration of the hydrogen source 2-propanol is high, (S)-phenylethanol and (R)-phenylethanol are produced in the reaction system in a ratio of 99:1. However, when the reaction proceeds and the concentration of (S)-phenylethanol is increased, the reverse reaction will reduce the composition ratio (optical purity) of (S)- and (R)-phenylethanols in the reaction system; their ratio will be reduced to 97:3 at 75% conversion. As being such an equilibrium reaction, in a reaction system where 2-propanol is employed as hydrogen source, in order to obtain an optically active alcohol in high optical purity, there have been problems that there must be a large excessive amount of the hydrogen source 2-propanol than the product optically active alcohol; and that the reaction must be carried out under the condition where the concentration of the ketone substrate is as low as approximately 0.1M.

In order to solve these problems, in Non-patent Literature 2, formic acid is used as the hydrogen source. In this method, formic acid is eliminated from the system as carbon dioxide after providing hydrogen, rendering the reaction irreversible and increasing the optical purity of the produced optically active alcohol. Although using this method, the optical purity and the S/C ratio (substrate/catalyst molar ratio) of the optically active alcohol were improved compared to the reaction using 2-propanol as the hydrogen source, there still is a necessity of improvement, such as in the S/C ratio (substrate/catalyst molar ratio).

Then Non-patent Literature 3 suggested a method to use sodium formate as the hydrogen source under a condition of a two-phase reaction system where water is employed as the solvent. In this method, although there is a large increase in the reaction rate and an improvement in the S/C ratio (substrate/catalyst molar ratio) compared to the reaction using formic acid, the optical purity of the alcohol is decreased. For example, a reaction of an acetophenone gives phenylethanol at 97% ee using formic acid, whereas a two-phase reaction system gives phenylethanol at 95% ee.

Meanwhile, a high catalytic activity of the two-phase reaction system is interpreted to be an effect exhibited by water (Non-patent Literatures 3 and 4), and therefore, in Non-patent Literature 5, many of the approaches for achieving a high optical purity were focused on the structural optimization of the catalyst and the development of an aqueous catalyst, while leaving the condition unchanged that water is present. On the other hand, Non-patent Literature 6 reported as an approach to improve the reacting conditions, a homogenous reaction system in which potassium formate in polyethyleneglycol is used as a hydrogen source. This approach, however, is focused on the recycle of catalyst by retaining the catalyst in polyethyleneglycol phase, and there is no mentioning about any suppressive effect on the racemization of the produced alcohol by the homogenous reaction.

CITATION LIST

Patent Literatures

[Patent Literature 1] JP B No. 2962668
[Patent Literature 2] JP B No. 4090078

Non-patent Literatures

[Non-patent Literature 1] S. Hashiguchi, A. Fujii, J. Takehara, T. Ikariya, R. Noyori, J. Am. Chem. Soc. 1995, 117, 7562
[Non-patent Literature 2] A. Fujii, S. Hashiguchi, N. Uematsu, T. Ikariya, R. Noyori, J. Am. Chem. Soc. 1996, 118, 2521
[Non-patent Literature 3] X. Wu, X. Li, W. Hems, F. Hems, F. King, J. Xiao, Org. Biomol. Chem. 2004, 2, 1818
[Non-patent Literature 4] X. Wu, C. Wang, J. Xiao, Platiunm Metals Rev. 2010, 54, 3
[Non-patent Literature 5] C. Wang, X. Wu, J. Xiao, Chem. Asian, J. 2008, 3, 1750
[Non-patent Literature 6] H. F. Zhou, Q. H. Fan, Y. Y. Huang, L. Wu, Y. M. He, W. J. Tang, L. Q. Gu, A. S. C. Chan, J. Mol. Catal. A: Chem. 2007, 275, 47

SUMMARY OF THE INVENTION

Problems to be Solved by the Invention

Accordingly, an object of the present invention is to solve the problems in the prior arts, and to find a more improved reaction conditions for suppressing the racemization of the product and obtaining an optically active alcohol at a high optical purity.

Means for Solving the Problems

In view of the present circumstances as above, the inventors, through an intensive study for solving above problems, focused not on the tuning of a catalyst but on the optimization of reaction conditions, because changing ligand structure would increase the cost of the catalyst. The inventors then focused on the fact that the optical purity was decreased to 95% ee in the two-phase reaction system of the Non-patent Literature 3 above compared to 97% ee of the Non-patent Literature 2, and then sought for the meanings of this small decrease in optical purity, which was of little interest at the time. Accordingly, the inventors actually carried out reactions using various ketone substrates, and from the results reached the recognition that the type of ketone is a important problem in a two-phase reaction system because the optical purity is decreased by more than 5% ee depending on the type of ketone.

Under this recognition, the inventors further pursued the study and reached the speculation that the reduction in the optical purity of the optically active alcohol produced in a two-phase reaction system is caused as follows: because the produced optically active alcohol and catalyst are in an organic phase whereas the hydrogen source is present in an aqueous phase, the hydrogen source supplied to the catalyst is insufficient during the later reaction, accelerating the dehydrogenation of the optically active alcohol that present nearby the catalyst, resulting in the decrease in the optical purity according to the reaction mechanism described as above. Such an speculation was consistent with the increase in the rate of the racemization when decreasing the stirring rate. Thus, the inventors considered that the problem of the racemization of the optically active alcohol in the two-phase reaction system may be solved, if we could make an asymmetric catalyst and hydrogen source exist in the same phase using a solvent system that is capable of resolving both the formate salt and the asymmetric catalyst, and as a result of further researches completed the invention.

Namely, the present invention is a process for producing an optically active alcohol by reacting a ketone substrate in a solvent(s) using a hydrogen source in the presence of an asymmetric catalyst, wherein:
the asymmetric catalyst is a metal complex represented by the following general formula (I):

[Chem.1]

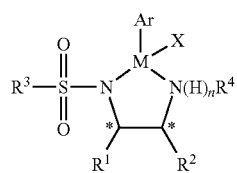

(1)

wherein,
$R^1$ and $R^2$ may be identical or different to each other, and is a hydrogen atom, an alkyl group, a phenyl group which may have one or more substituents, a naphthyl group which may have one or more substituents or a cycloalkyl group which may have one or more substituents, or $R^1$ and
$R^2$ are bound together to form an alicyclic ring which is unsubstituted or have one or more substituents,
$R^3$ is an alkyl group, a perfluoroalkyl group, a naphthyl group which may have one or more substituents, a benzyl group which may have one or more substituents, a phenyl group which may have one or more substituents or a camphor group which may have one or more substituents,
$R^4$ is a hydrogen atom or an alkyl group,
Ar is a benzene which may have one or more substituents or a cyclopentadienyl group which may have one or more substituents,
X is an anionic group,
M is ruthenium, rhodium or iridium,
n denotes 0 or 1, where X is not present when n=0,
* denotes an asymmetric carbon;
the hydrogen source is a formate salt; and
the solvent(s), which is(are) capable of dissolving the asymmetric catalyst and the formate salt, is(are) (1) an organic solvent(s) (except polyethylenglycol) and/or (2) an organic solvent(s) (except polyethyleneglycol) and/or a water-miscible aprotic solvent(s), and water.

The invention further relates to said process for producing the optically active alcohol, wherein the organic solvent(s) is(are) a protic solvent(s).

The invention also relates to said process for producing the optically active alcohol, wherein the organic solvent(s) is(are) an alcohol having 1 to 5 carbon atoms.

The invention further related to said process for producing the optically active alcohol, wherein the organic solvent(s) is(are) methanol and/or ethanol.

The invention also related to said process for producing the optically active alcohol, wherein the aprotic solvent(s) is(are) DMF (dimethylformamide) and/or DMSO (dimethylsulfoxide).

The invention further relates to said process for producing the optically active alcohol, wherein the solvent(s) comprise(s) an organic solvent(s) (excluding polyethyleneglycol) and water.

The invention also related to said process for producing the optically active alcohol, wherein the solvent(s) comprise(s) an organic solvent(s) (excluding polyethyleneglycol) and an aprotic solvent(s).

The invention further relates to said process for producing the optically active alcohol, wherein the solvent(s) comprise(s) water and a water-miscible aprotic solvent(s).

The invention also relates to said process for producing an optically active alcohol, wherein the solvent(s) comprise(s) an organic solvent(s) (except polyethyleneglycol), water-miscible aprotic solvent(s) and water.

The invention further relates to said process for producing the optically active alcohol, wherein the formate salt is potassium formate and/or sodium formate.

The invention also related to said process for producing the optically active alcohol, wherein the ketone substrate is a cyclic ketone, a ketone having an olefin moiety, a ketone having an acetylene moiety, a ketone having a hydroxyl group, a ketone having a halogen atom, a diketone, a ketoester or a ketoamide.

The invention further relates to said process for producing the optically active alcohol, wherein the reaction is performed in a homogenous phase.

Also, the invention may be, in one of its embodiments, a process for producing an optically active alcohol by reacting a ketone substrate in a solvent(s) using a hydrogen source in the presence of an asymmetric catalyst, wherein
the asymmetric catalyst is metal complex represented by the following general formula (1):

[Chem.2]

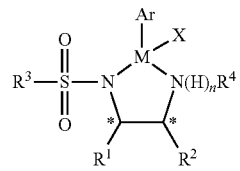

(1)

wherein,
$R^1$ and $R^2$ may be identical or different to each other, and is a hydrogen atom, an alkyl group, a phenyl group which may have one or more substituents, a naphthyl group which may have one or more substituents or a cycloalkyl group which may have one or more substituents, or $R^1$ and
$R^2$ are bound together to form an alicyclic ring which is unsubstituted or have one or more substituents,
$R^3$ is an alkyl group, a perfluoroalkyl group, a naphthyl group which may have one or more substituents, a benzyl group which may have one or more substituents, a phenyl group which may have one or more substituents or a camphor group which may have one or more substituents, $R^4$ is a hydrogen atom or an alkyl group, Ar is a benzene which may have one or more substituents or a cyclopentadienyl group which may have one or more substituents, X is an anionic group, M is ruthenium, rhodium or iridium, n denotes 0 or 1, where X is not present when n=0.

* denotes an asymmetric carbon, the hydrogen source is a formate salt, and the solvent(s), which is(are) capable of dissolving the asymmetric catalyst and the formate salt, is (1) an organic solvent(s) (except polyethyleneglycol) and/or (2) water and a water-miscible aprotic solvent(s).

Effects of the Invention

The present invention can solve the problems in the prior arts, suppress the racemization of the product, asymmetrically reduce various ketone substrates at a high efficiency, and give an optically active alcohol at a high purity. The present invention can further facilitate the purification of the produced optically active alcohol without requiring any complicated steps. The present invention can also give an extremely high purity of an optically active alcohol by known methods for purification, without using any special procedures for purification. Note that the aim of using a solvent(s) that is capable of resolving an asymmetric catalyst and a formate salt is to allow the asymmetric catalyst and the hydrogen source to be present within the same phase (existing as a homogenous phase), but not to use it as a hydrogen source.

Specifically, according to the invention, an optically active cyclic alcohol (reducing asymmetrically a cyclic ketone), an optically active alcohol having an olefin moiety or an acetylene moiety (reducing asymmetrically a ketone having an olefin moiety or an acetylene moiety (in particular, a ketone in which α,β-linkage is an olefin moiety or an acetylene moiety)), an optically active alcohol having a hydroxyl group (reducing asymmetrically a ketone having a hydroxyl group), an optically active alcohol having a halogen atom (reducing asymmetrically a ketone having a halogen atom (in particular, a ketone having a halogen atom at α-position)), an optically active chromanol (reducing asymmetrically a chromanone derivative), an optically active diol (reducing asymmetrically a diketone), an optically active hydroxy ester (reducing asymmetrically a ketoester), an optically active hydroxy amide (reducing asymmetrically a ketoamide) can be produced.

DESCRIPTION OF EMBODIMENTS

The process according to the invention to produce an optically active alcohol by reacting a ketone substrate in a solvent(s) using a hydrogen source in the presence of an asymmetric catalyst is to be performed in a solvent(s) that is capable of resolving the asymmetric catalyst and the formate salt.

The asymmetric catalyst used in the method according to the invention is not particularly limited as long as it is capable of asymmetrically reducing a ketone substrate to an optically active alcohol, though it typically is represented by the following general formula (1):

[Chem.3]

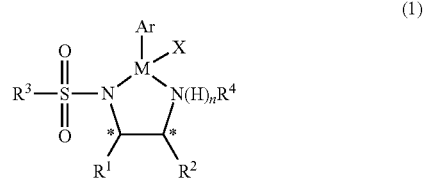

In the general formula (1), $R^1$ and $R^2$ are, for example, a hydrogen atom, an alkyl group having 1 to 10 carbon atoms, an unsubstituted phenyl group, a phenyl group having an alkyl group having 1 to 5 carbon atoms, a phenyl group having a halogen atom, a phenyl group having an alkoxy group, a naphthyl group which may have one or more substituents and a cycloalkyl group having 3 to 10 carbon atoms, or $R^1$ and $R^2$ are bound to each other to form an alicyclic ring which either is unsubstituted or has one or more substituents.

The alkyl group having 1 to 10 carbon atoms is such as, for example, a methyl group, ethyl group, n-propyl group, iso-propyl group, n-butyl group, sec-butyl group and tert-butyl group.

The phenyl group having an alkyl group having 1 to 5 carbon atoms is such as, for example, a 4-methylphenyl group and 3,5-dimethylphenyl group.

The phenyl group having a halogen atom is such as, for example, a 4-fluorophenyl group, 4-chlorophenyl group and 4-trifluoromethylphenyl group.

The phenyl group having an alkoxy group is such as, for example, 4-methoxyphenyl group, 4-ethoxyphenyl group, 4-methoxymethylphenyl group, 3-methoxyphenyl group, 3-ethoxyphenyl group, 3-methoxymethylphenyl group, 2-methoxyphenyl group, 2-ethoxyphenyl group and 2-methoxymethylphenyl group.

The naphthyl group which may have one or more substituents is such as, for example, an unsubstituted naphthyl group, 5,6,7,8-tetrahydro-1-naphthyl group and 5,6,7,8-tetrahydro-2-naphthyl group.

The cycloalkyl group having 3 to 10 carbon atoms is such as, for example, a cyclopropyl group, a cyclopentyl group and a cyclohexyl group.

The alicyclic ring which $R^1$ and $R^2$ are bound together to form a ring and which is unsubstituted or have one or more substituents is such as, for example, a cyclopentane ring or a cyclohexane ring which is formed by $R^1$ and $R^2$ bound together to form a ring.

Among these, from the viewpoint of being readily-synthesized and commercially available, the substituents for $R^1$ and $R^2$ is preferably a hydrogen atom, a phenyl group which may have one or more substituents, a cyclohexane ring formed by $R^1$ and $R^2$ bound together to form a ring, more preferably $R^1$ and $R^2$ are both phenyl groups or bound together to form a cyclohexane.

In the general formula (1), $R^3$ is such as, for example, an alkyl group having 1 to 10 carbon atoms, a cycloalkyl group having 3 to 10 carbon atoms, a benzyl group which may have one or more substituents, a naphthyl group which may have one or more substituents, a phenyl group which may have one or more substituents, and a camphor group which may have one or more substituents.

The alkyl group having 1 to 10 carbon atoms is such as, for example, a methyl group, ethyl group, n-propyl group, iso-propyl group, n-butyl group, sec-butyl group, and tert-butyl group, and the alkyl group may further have one or more substituents, such as, for example, one or more fluorine atoms as a substituent. The alkyl group comprising one or more fluorine atoms is such as, for example, a fluoromethyl group, difluoromethyl group, trifluoromethyl group and a pentafluoroethyl group.

The cycloalkyl group having 3 to 10 carbon atoms is such as, for example, a cyclopropyl group, a cyclopentyl group and a cyclohexyl group.

The benzyl group which may have one or more substituents is such as, for example, an unsubstituted benzyl group and 2,6-dimethylbenzyl group.

The naphthyl group which may have one or more substituents is such as, for example, an unsubstituted naphthyl group, 5,6,7,8-tetrahydro-1-naphthyl group, and 5,6,7,8-tetrahydro-2-naphthyl group.

The phenyl group which may have one or more substituents is such as, for example, an unsubstituted phenyl group, a phenyl group having an alkyl group such as a 4-methylphenyl group, 3,5-dimethylphenyl group, 2,4,6-trimethylphenyl group and 2,4,6-triisopropylphenyl group, a phenyl group having a halogen atom such as a 4-fluorophenyl group, 4-chlorophenyl group and 2,4,6-trichlorophenyl group, a phenyl group having an alkoxy group such as a 4-methoxyphenyl group, and a camphor group which may have one or more substituents.

In the general formula (1), $R^4$ is such as, for example, an alkyl group having 1 to 5 carbon atoms such as a methyl group and an ethyl group, and a hydrogen atom.

Among these, from the viewpoint of obtaining a high catalytic activity, $R^4$ is preferably a methyl group or a hydrogen atom, more preferably a hydrogen atom.

In the general formula (1), Ar is such as, for example, an unsubstituted benzene, a benzene having an alkyl group, and a cyclopentadienyl group which may have one or more substituents.

The benzene having an alkyl group is such as, for example, toluene, o—, m— and p-xylene, o—, m—and p-cymene, 1,2,3-, 1,2,4-, and 1,3,5-trimethylbenzene, 1,2,4,5-tetramethylbenzene, 1,2,3,4-tetramethylbenzene, pentamethylbenzene, and hexamethylbenzene.

The cyclopentadienyl group which may have one or more substituents is such as, for example, a cyclopentadienyl group, methylcyclopentadienyl group, 1,2-dimethylcyclopentadienyl group, 1,3-dimethylcyclopentadienyl group, 1,2,3-trimethylcyclopentadienyl group, 1,2,4-trimethylcyclopentadienyl group, 1,2,3,4-tetramethylcyclopentadienyl group and 1,2,3,4,5-pentamethylcyclopentadienyl group.

Among these, from the viewpoint of giving a high asymmetric yield and the availability of the ingredient materials, Ar is preferably a p-cymene, 1,3,5-trimethylbenzene, 1,2,4,5-tetramethylbenzene, hexamethylbenzene or 1,2,3,4,5-pentamethylcyclopentadiene, and more preferably a p-cymene, 1,3,5-trimethylbenzene or 1,2,3,4,5-pentamethylcyclopentadiene.

In the general formula (1), X is, for example an anionic group, and an anionic group herein includes a halogen atom.

The anionic group is such as, for example, fluorine atom, chlorine atom, bromine atom, iodine atom, tetrafluoroborate group, tetrahydroborate group, tetrakis[3,5-bis(trifluoromethyl)phenyl]borate group, acetoxy group, benzoyloxy group, (2,6-dihydroxybenzoyl)oxy group, (2,5-dihydroxybenzoyl)oxy group, (3-aminobenzoyl)oxy group, (2,6-dimethoxybenzoyl)oxy group, (2,4,6-triisopropylbenzoyl)oxy group, 1-naphthalene carboxylic acid group, 2-naphthalene carboxylic acid group, trifluoroacetoxy group, trifluoromethanesulfoxy group and trifluoromethanesulfonimide group.

Among these, from the viewpoint of the availability of the ingredient materials, an anionic group is preferably a chlorine atom, bromine atom, iodine atom or trifluoromethanesulfoxy group, more preferably a chlorine atom or trifluoromethanesulfoxy group.

In the general formula (1), M is such as, for example, ruthenium, rhodium and iridium.

Among these, in view of the cost, M is preferably ruthenium or iridium.

The metal complex represented by the general formula (1) has a structure in which a bidentate ligand, ethylenediamine derivative or cyclohexanediamine derivative, (a ligand of the general formula (1): $R^3SO_2NHCHR^1CHR^2NHR^4$) is coordinated to ruthenium, rhodium or iridium. Because the structure of the ligand that gives a high reactivity or asymmetric yield varies depending on the structure of the substrate, an optimum ethylenediamine derivative or cyclohexanediamine derivative may be selected in accordance with the structure of the substrate.

The ethylenediamine derivative is, though not particularly limited, such as, for example, TsDPEN(N-(p-toluenesulfonyl)-1,2-diphenyl ethylenediamine), MsDPEN (N-methanesulfonyl-1,2-diphenyl ethylenediamine), N-(benzylsulfonyl)-1,2-diphenyl ethylenediamine, N-(cyclohexanesulfonyl)-1,2-diphenyl ethylenediamine, N-(2,5-dimethylbenzylsulfonyl)-1,2-diphenyl ethylenediamine, N-(iso-butylsulfonyl)-1,2-diphenyl ethylenediamine, N-methyl-N'-(p-toluenesulfonyl)-1,2-diphenyl ethylenediamine, N-(p-methoxyphenylsulfonyl)-1,2-diphenyl ethylenediamine, N-(p-chlorophenylsulfonyl)-1,2-diphenyl ethylenediamine, N-trifluoromethanesulfonyl-1,2-diphenyl ethylenediamine, N-(2,4,6-trimethylbenzenesulfonyl)-1,2-diphenyl ethylenediamine, N-(2,4,6-triisopropylbenzenesulfonyl)-1,2-diphenyl ethylenediamine, N-(4-tert-butylbenzenesulfonyl)-1,2-diphenyl ethylenediamine, N-(2-naphthylsulfonyl)-1,2-diphenyl ethylenediamine, N-(3,5-dimethylbenzenesulfonyl)-1,2-diphenyl ethylenediamine, N-pentamethylbenzenesulfonyl-1,2-diphenyl ethylenediamine, N-(10-camphorsulfonyl)-1,2-diphenyl ethylenediamine, N-(benzylsulfonyl)-1,2-ethanediamine and N-(sec-butylsulfonyl)-1,2-ethanediamine.

These ethylenediamine derivatives are selected according to the structure of the ketone substrate. They are preferably, from the viewpoint of the general use, TsDPEN and MsDPEN, and from the viewpoint of obtaining a relatively high asymmetric yield in reactions of various ketones, ethylenediamine derivatives, such as N-(benzylsulfonyl)-1,2-diphenylethylenediamine, N-(cyclohexanesulfonyl)-1,2-diphenylethylenediamine, N-(2,5-dimethylbenzylsulfonyl)-1,2-diphenylethylenediamine, and N-(iso-butylsulfonyl)-1,2-diphenylethylenediamine.

The cyclohexanediamine derivative is, though not particularly limited, such as, for example, TsCYDN(N-(p-toluenesulfonyl)-1,2-cyclohexanediamine), MsCYDN (N-(p-methanesulfonyl)-1,2-cyclohexanediamine), N-(benzylsulfonyl)-1,2-cyclohexanediamine, N-(cyclohexanesulfonyl)-1,2-cyclohexanediamine, N-(cyclohexanesulfonyl)-1,2-cyclohexanediamine, N-(2,5-dimethylbenzylsulfonyl)-1,2-cyclohexanediamine, N-(iso-butylsulfonyl)-1,2-cyclohexanediamine, N-methyl-N'-(p-toluenesulfonyl)-1,2-cyclohexanediamine, N-(p-methoxyphenylsulfonyl)-1,2-cyclohexanediamine, N-(p-chlorophenylsulfonyl)-1,2-cyclohexanediamine, N-trifluoromethanesulfonyl-1,2-cyclohexanediamine, N-(2,4,6-trimethylbenzenesulfonyl)-1,2-cyclohexanediamine, N-(2,4,6-triisopropylbenzenesulfonyl)-1,2-cyclohexanediamine, N-(4-tert-butylbenzenesulfonyl)-1,2-cyclohexanediamine, N-(2-naphthylsulfonyl)-1,2-cyclohexanediamine, N-(3,5-dimethylbenzenesulfonyl)-1,2-cyclohexanediamine, N-pentamethylbenzenesulfonyl-1,2-cyclohexanediamine, N-(p-toluenesulfonyl)-1,2-cyclohexanediamine, and N-(10-camphorsulfonyl)-1,2-cyclohexanediamine.

These cyclohexanediamine derivatives are selected according to the structure of the ketone substrate. They are preferably, from the viewpoint of the general use, TsCYDN and MsCYDN, and from the viewpoint of obtaining a relatively high asymmetric yield in reactions of various ketones, ethylenediamine derivatives, such as N-(benzylsulfonyl)-1,2-cyclohexanediamine, N-(iso-butylsulfonyl)-1,2-cyclohexanesulfonyl)-1,2-cyclohexanediamine, and N-(2,5-dimethylbenzylsulfonyl)-1,2-cyclohexanediamine are preferred.

The ruthenium compound that is used as a starting material of the ruthenium complex represented by the general formula (1) is such as, for example, an inorganic ruthenium compound such as ruthenium (III) chloride hydrate, ruthenium (III) bromide hydrate and ruthenium (III) iodide hydrate; a ruthenium complex in which a diene is coordinated such as [ruthenium dichloride (norbornadiene)] poly-nuclear complex, [ruthenium dichloride (cycloocta-1,5-diene)] poly-nuclear complex and bis(methylallyl) ruthenium (cycloocta-1,5-diene); a ruthenium complex in which an aromatic compound is coordinated such as [ruthenium dichloride (benzene)] poly-nuclear complex, [ruthenium dichloride (p-cymene)] poly-nuclear complex, [ruthenium dichloride (trimethylbenzene)] poly-nuclear complex and [ruthenium dichloride (hexamethylbenzene)] poly-nuclear complex; a ruthenium complex in which a phosphine is coordinated such as dichlorotris(triphenylphosphine) ruthenium, as well as ruthenium dichloride (dimethylformamide)$_4$, and chlorohydride tris(triphenylphosphine) ruthenium.

In addition, a ruthenium complex is not particularly limited to the above as long as it has a ligand that is capable of being substituted with an optically active diphosphine compound or optically active diamine compound. For example, various ruthenium complexes described in COMPREHENSIVE ORGANOMETALLIC CHEMISTRY II Vol. 7 p 294-296 (PERGAMON) may be used as a starting material.

Similarly, a rhodium compound that can be used as a starting material for the rhodium complex represented by the general formula (I) is, for example, an inorganic rhodium compound such as rhodium (III) chloride hydrate, rhodium (III) bromide hydrate and rhodium (III) iodide hydrate, as well as [pentamethylcyclopentadienyl rhodium dichloride] poly-nuclear complex, [pentamethylcyclopentadienyl rhodium dibromide] poly-nuclear complex and [pentamethylcyclopentadienyl rhodium diiodide] poly-nuclear complex. An iridium compound that can be used as a starting material for the iridium complex represented by the general formula (I) is, for example, an inorgaganic iridium compound such as iridium (III) chloride hydrate, iridium (III) bromide hydrate and iridium (III) iodide hydrate, as well as [pentamethylcyclopentadienyl iridium dichloride] poly-nuclear complex, [pentamethyl cyclopentadienyl iridium dibromide] poly-nuclear complex and [pentamethyl cyclopentadienyl iridium diiodide] poly-nuclear complex.

The reaction of the stating material ruthenium, rhodium or iridium compounds with the ligand is performed in one or more solvents selected from the group consisting of aromatic hydrocarbon solvents such as toluene and xylene, aliphatic hydrocarbon solvents such as pentane and hexane, halogen-containing hydrocarbon solvents such as methylene chloride, ether solvents such as diethyl ether and tetrahydrofuran, alcoholic solvents such as methanol, ethanol, 2-propanol, butanol and benzylalcohol, and organic solvents containing heteroatoms such as acetonitrile, DMF (dimethylformamide), N-methylpyrrolidone and DMSO (dimethylsulfoxide), at a reaction temperature between 0° C. to 200° C. A metal complex which is an asymmetric catalyst to be used in the method according to the invention, can be obtained by the above reaction.

In order to obtain an optically active alcohol it is necessary that the two asymmetric carbons in the metal complex represented by the general formula (1) used as an asymmetric catalyst in the method according to the invention are either both (R) enantiomers or both (S) enantiomers. Selecting either of these (R) enantiomer and (S) enantiomer enables a high selectivity for the optically active alcohol of desired absolute configuration. These metal complexes may be used alone or in combination of two or more.

The amount of the metal complex used in the method according to the invention represented by the general formula (1) may be in the range from 10 to 20,000 S/C, as expressed by the molar ratio of the ketone substrate to that of the metal complex, i.e., S/C (wherein S indicates the substrate and C indicates the catalyst). Within this range, from the viewpoint of reaction efficiency and economic efficiency, it is preferably in the range from 100 to 10,000, more preferably in the range from 1,000 to 10,000.

The solvent(s) used in the method according to the invenntion that is capable of resolving the asymmetric catalyst and formate salt is not limited to its type, as long as the solvent(s) is capable of resolving the metal complex, i.e., an asymmetric catalyst, and the formate salt, and is, for example, organic solvents such as a protic solvent(s), an organic acid and an ionic liquid except polyethylene glycol, and a mixed solvent of water and an water-miscible aprotic solvent(s). The organic solvent(s) may further comprise water and an water-miscible aprotic solvent(s).

The protic solvent(s) is(are) such as aliphatic alcohols, multivalent alcohols and organic acids, among which a protic solvent(s) having 1 to 5 carbon atoms is(are) preferred. These protic solvents may also be used alone or in a combination of two or more.

The aliphatic alcohol is such as, for example, methanol, ethanol, 2-propanol, n-propyl alcohol, 2-methyl-2-propanol and 2-methyl-2-butanol. Among these, from the viewpoint of high reactivity due to high solubility of the formate salt, preferred is an alcohol having 1 to 5 carbon atoms, and more preferred is methanol or ethanol, and most preferred is methanol.

The polyalcohol is such as, for example, ethylene glycol, glycerin and propylene glycol.

The organic acid is such as, formic acid, acetic acid, propionic acid and trifluoroacetic acid.

The ionic liquid is, such as, an ionic liquid comprising an imidazolium as a cation such as 1-ethyl-3-methylimidazolium bromide, 1-ethyl-3-methylimidazolium hexafluorophosphate and 1-butyl-3-methylimidazolium trifluoromethane sulfonate, an ionic liquid comprising a pyridinium as a cation such as 1-ethylpyridinium bromide and 1-hexylpyridinium tetrafluoroborate, an ionic liquid comprising a quaternary ammonium as a cation such as N,N,N-trimethyl-N-propylammonium bis(trifluoromethane sulfonyl)imide, and an ionic liquid comprising phosphonium as a cation such as (1-naphthyl)triphenylphosphonium chloride.

The water-miscible aprotic solvent(s) is(are) not limited to its type, as long as it is(they are) a solvent(s) miscible with water and capable of resolving the metal complex, i.e., the asymmetric catalyst, and the formate salt, and is such as, for example, DMF (dimethylformamide), DMSO (dimethylsulfoxide), THF (tetrahydrofuran), 1,4-dioxane, acetonitrile and pyridine. These aprotic solvents may be used alone or in combination of two or more.

The ketone substrate used in the method according to the invention is such as, for example, a cyclic ketone, a ketone having an olefin moiety, a ketone having an acetylene moiety, a ketone having a hydroxyl group, a ketone having a halogen atom, a diketone, a ketoester and a ketoamide, which may have one or more substituents having a π (pi) electron, for example an aromatic ring, a heteroaromatic ring, a carbon-carbon triple bond, a carbon-carbon double bond, nearby the carbonyl group, or other substituents including a carboxylic acid group, an ester group, a carboxylic amide group, a carbonyl group, an amino group, an amide group, a cyano group, a nitro group, a chlorine group, a bromine group, an iodine group, a trifluoromethyl group, a hydroxyl group, an alkoxy group, a thiol group, a trimethylsilyl group, a tert-butyldimethylsilyl group, and other substituents comprising heteroatoms.

The process for producing an optically active alcohol described in the present invention is effective for the reaction of ketone substrates having various substituents. There is no need for particularly limiting the structure of a ketone substrate, though it is such as, for example, as an aromatic ketone, acetophenone, propiophenone, 3'-chloroacetophenone, 2'-trifluoromethylacetophenone, 3',5'-bis(trifluoromethyl)acetophenone and 3'-hydroxyacetophenone. A cyclic ketone is such as 4-chromanone, 1-indanone and 1-tetralone. A ketone having other functional groups is phenacyl chloride, α-hydroxyacetophenone, benzoin, α-nitroacetophenone, α-cyanoacetophenone, α-azideacetophenone, α-(methoxycarbonyl)acetophenone, α-(ethoxycarbonyl)acetophenone, 1-(tert-butyldimethylsilyl)-1-butyn-3-one and 1-(trimethylsilyl)-1-butyn-3-one.

The formate salt used as a hydrogen source to supply hydrogen atoms to a ketone substrate is such as, for example, a salt of formic acid and an alkali metal or an alkali earth metal, which may be used alone or in combination of two or more.

The salt of formic acid and an alkali metal or an alkali earth metal is such as, for example, lithium formate, sodium formate, potassium formate, cesium formate, magnesium formate and calcium formate. Among these, from the viewpoint of a high reactivity, a salt of formic acid and an alkali metal or an alkali earth metal is preferably potassium formate or sodium formate, more preferably potassium formate.

Furthermore, in the method according to the inventino, an acid or base may be added as required. An acid to be added is, though not particularly limited, for example, organic acids such as formic acid and acetic acid. A base is inorganic basic compounds such as potassium hydroxide, sodium hydroxide, potassium carbonate, sodium carbonate, potassium hydrogencarbonate and sodium hydrogencarbonate, or organic basic compounds such as triethylamine and DBU. These acids and bases may be used alone or in combination of two or more, and the mixture thereof may be used for the asymmetric reduction reaction of a ketone substrate.

The reaction temperature is, though not particularly limited, in view of the economic efficiency, preferably in the range from 0 to 70° C., more preferably from 20 to 60° C.

The reaction time varies depending on the reaction conditions such as the types, concentration or S/C of the reacting substrates or temperature, or the type of the catalyst. Therefore, the various conditions may be determined so as to allow the reaction to be finished in several minutes to several days, preferably, in particular, in 5 to 24 hours.

The purification method of the reaction product, i.e., optically active alcohol, is not particularly limited. For instance, a known method such as column chromatography, distillation and recrystallization may be employed.

The asymmetric reduction reaction of the ketone substrate in the process of the present invention may also be performed in a reaction type of either a batch type or continuous type.

EXAMPLES

The followings describe the working examples and comparative examples of the present invention to illustrate the present invention in more detail, though the present invention is not limited by these working examples.

In the working examples below, the solvent(s) used for the reactions was(were) purchased reagents. The identification of the product was performed by nuclear magnetic resonance (NMR) spectroscopy using JNM-LA400 (400 MHz, JEOL Ltd.). Tetramethylsilane (TMS) was used as an internal standard substance for the measurement by $^1$HNMR, and its signal was determined as δ=0 (δ is a chemical shift). The optical purity was measured by gas chromatography (GC) or high-performance liquid chromatography (HPLC). Chirasil-DEX CB (0.25 mm×25 m, DF=0.25 µm) (CHROMPACK, Inc.) was used for GC, and CHIRALCEL OD (0.46 cm×25 cm), CHIRALCEL OJ (0.46 cm×25 cm), CHIRALCEL OB-H (0.46 cm×25 cm) and CHIRALCEL OJ-H (0.46 cm×25 cm) (DAICEL CHEMICAL INDUSTRIES, LTD.) were used for HPLC.

Working Example 1

A ruthenium complex RuCl[(R,R)-Tsdpen] (p-cymene) (6.4 mg, 0.01 mmol), potassium formate (1.0 g, 12 mmol) and 4-chromanone (1.48 g, 10 mmol, substrate/catalyst ratio=1,000) were set in a 20 mL glass Schlenk-type reaction tube under an argon atmosphere. Methanol (6 mL) was added thereto and stirred at 50° C. After reacting for 3 hours, the yield of (R)-4-chromanol was 99%, and the optical purity was 99% ee. The reaction was allowed to further continue to give, after 6 hours, a yield of 100% and optical purity of 99% ee. After 24 hours, (R)-4-chromanol was produced at 100% yield and 99% ee optical purity.

This confirmed that the racemization of (R)-4-chromanol did not proceed over time in this reaction system.

Comparative Example 1

A ruthenium complex RuCl[(R,R)-Tsdpen] (p-cymene) (6.4 mg, 0.01 mmol), TBAB (tetrabutylammonium bromide) (32.2 mg, 0.1 mmol), potassium formate (1.0 g, 12 mmol) and 4-chromanone (1.48 g, 10 mmol, substrate/catalyst ratio=1,000) were set in a 20 mL glass Schlenk-type reaction tube under an argon atmosphere. Water (2 mL) and toluene (2 mL) were added thereto and stirred at 50° C. After reacting for 3 hours, the yield of the product (R)-4-chromanol was 90%, and the optical purity was 92% ee. The reaction was allowed to further continue to give, after 6 hours, a yield of 99% and optical purity of 92% ee. After 24 hours, (R)-4-chromanol was produced at 99% yield and 90% ee optical purity.

This confirmed that the racemization of (R)-4-chromanol proceeded over time in the two-phase reduction reaction system.

Comparative Example 2

Argon was introduced into a 20 mL Schlenk-type reaction tube and bathed in an ice bath, then triethyl amine (3.6 mL, 26 mmol), formic acid (1.2 mL, 31 mmol), 4-chromanone (1.48 g, 10 mmol, substrate/catalyst ratio=500) and ruthenium complex RuCl[(R,R)-Tsdpen] (p-cymene) (12.7 mg, 0.02 mmol) were set therein, stirred at 30° C. for 24 hours. On its course, samples were collected after 3 hours for $^1$HNMR and HPLC analyses of the product. The conversion rate after 3 hours was 66%, and the optical purity was 99% ee. The reaction was allowed to further continue, and after 24 hours, (R)-4-chromanol was produced at 100% yield of and 99% ee optical purity.

This confirmed that the reaction efficiency was low, though the racemization of (R)-4-chromanol did not proceed over time in the formic acid reaction system.

Working Examples 2-7

The reaction was performed to synthesize (R)-4-chromanol under similar conditions to those of Working Example 1 at 50° C. and for 24 hours, except changing the solvent(s) and the types of the hydrogen source, i.e., formate salt. The results are summarized in Table 1.

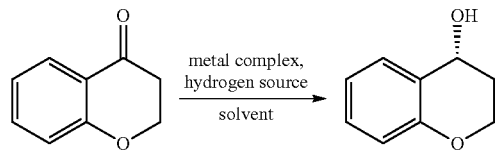

[Chem. 4]

TABLE 1

| Working Example | Solvent(s) | | Formate salt | Yield (%) | Optical purity (% ee) |
|---|---|---|---|---|---|
| 2 | 4 mL methanol 2 mL water | — | potassium formate | 100 | 98.6 |
| 3 | 4 mL methanol 2 mL water | — | sodium formate | 100 | 98.8 |
| 4 | 5 mL methanol | DMF 1 mL | potassium formate | 100 | 99.1 |
| 5 | 6 mL methanol 2 mL water | — | potassium formate | 100 | 98.4 |
| 6 | 2 mL water | DMSO 5 mL | potassium formate | 100 | 97.8 |
| 7 | 2 mL water | DMF 5 mL | potassium formate | 100 | 97.8 |

Working Examples 8-13

The reaction was performed to synthesize (R)-4-chromanol under a similar conditions to those of Working Example 1 at 50° C. and for 24 hours, except using RuCl[(R,R)-Tsdpen] (p-cymene) to perform the reaction at a higher S/C, or changing the catalyst to be used. The results are summarized in Table 2. Note that, in Working Example 9, the reaction solvent was a mixed solvent of 4 mL methanol and 2 mL water.

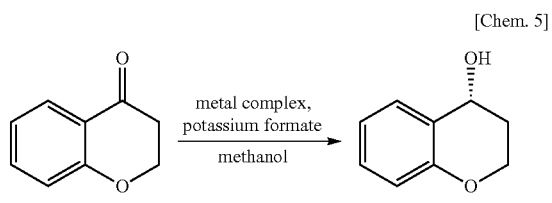 [SMILES: O=C1CCOc2ccccc21 ; O[C@@H]1CCOc2ccccc21]

[Chem. 5]

TABLE 2

| Working Example | S/C | Catalyst | Yield (%) | Optical purity (% ee) |
|---|---|---|---|---|
| 8 | 5000 | RuCl[(R,R)-Tsdpen](p-cymene) 1.3 mg (0.002 mmol) | 86 | 99.2 |
| 9 | 5000 | RuCl[(R,R)-Tsdpen](p-cymene) 1.3 mg (0.002 mmol) | 95 | 98.6 |
| 10 | 1000 | Ru(OTf)[(R,R)-Tscydn](p-cymene) 6.5 mg (0.01 mmol) | 100 | 95.9 |
| 11 | 1000 | Ru(OTf) [(R)-Cs-(R,R)-dpen](mesitylene) 7.9 mg (0.01 mmol) | 100 | 99.5 |
| 12 | 1000 | Cp*Ir(OTf)[(S,S)-Msdpen] 7.6 mg (0.01 mmol) | 100 | 99.7 |
| 13 | 1000 | Cp*RhCl[(S,S)-Msdpen] 5.6 mg (0.01 mmol) | 100 | 99.9 |

Working Example 14

A ruthenium complex RuCl[(R,R)-Tsdpen] (p-cymene) (6.4 mg, 0.01 mmol), potassium formate (1.0 g, 12 mmol) and acetophenone (1.20 g, 10 mmol, substrate/catalyst ratio=1000) were set in a 20 mL glass Schlenk-type reaction tube under an argon atmosphere. Methanol (6 mL) was added thereto and stirred at 50° C. for 24 hours to give (R)-1-phenylethanol at 100% yield and 96.2% ee optical purity.

Working Examples 15-20

The reaction was performed to synthesize each optically active alcohol under a similar condition to those of Working Example 14 except changing the ketone substrate. The results are summarized in Table 3. Note that, in Working Example 15, the reaction temperature was set at 30° C., and, in Working Example 19, the reaction was performed for 16 hours.

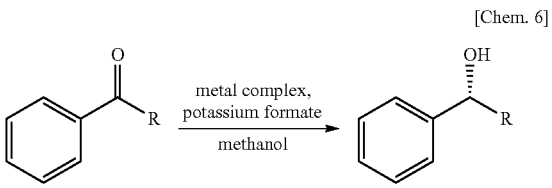

[Chem. 6]

TABLE 3

| Working Example | R | Yield (%) | Optical purity (% ee) |
|---|---|---|---|
| 15 | $CH_2Cl$ 1.55 g (10 mmol) | 99 | 97.8 |
| 16 | $CH_2OH$ 1.36 g (10 mmol) | 100 | 94.6 |
| 17 | $CH_2CN$ 1.45 g (10 mmol) | 91 | 95.4 |
| 18 | CH(OH)Ph 2.12 g (10 mmol) | 74 | 100 |
| 19 | $CH_2CO_2CH_3$ 1.78 g (10 mmol) | 100 | 96.5 |
| 20 | $(CH_2)_2OH$ 1.52 g (10 mmol) | 59 | 93.4 |

Working Example 21

A ruthenium complex RuCl[(R,R)-Tsdpen] (mesitylene) (2.1 mg, 0.0033 mmol), potassium formate (1.0 g, 12 mmol), formic acid (138 mg, 3 mmol) and 3'-chloroacetophenone (1.55 g, 10 mmol, substrate/catalyst ratio=3000) were set in a 20 mL glass Schlenk-type reaction tube under an argon atmosphere. Methanol (6 mL) was added thereto and stirred at 50° C. for 24 hours to give (R)-1-(3'-chlorophenyl)ethanol at 100% yield and 96.5% ee optical purity.

Working Example 22

A ruthenium complex RuCl[(S,S)-BnSO$_2$dpen] (mesitylene) (1.2 mg, 0.002 mmol), potassium formate (1.0 g, 12 mmol), formic acid (138 mg, 3 mmol) and 3'-chloroacetophenone (1.55 g, 10 mmol, substrate/catalyst ratio=5000) were set in a 20 mL glass Schlenk-type reaction tube under an argon atmosphere. Methanol (6 mL) was added thereto and stirred at 50° C. for 24 hours to give (S)-1-(3'-chlorophenyl) ethanol at 85% yield and 96.5% ee optical purity.

Working Example 23

A ruthenium complex Ru(OTf)[(S,S)-iso-BuSO$_2$dpen] (p-cymene) (1.4 mg, 0.002 mmol), potassium formate (1.0 g, 12 mmol), and 3',5'-bis(trifluoromethyl)acetophenone (2.56 g, 10 mmol, substrate/catalyst ratio=5000) were set in a 20 mL glass Schlenk-type reaction tube under an argon atmosphere. Methanol (6 mL) was added thereto and stirred at 50° C. for 24 hours to give (S)-1-[3',5'-bis(trifluoromethyl)phenyl]ethanol at 100% yield and 87.7% ee optical purity.

Accordingly, the effect of the present invention is that it suppresses the racemization of the product while maintaining the high reactivity of the two-phase reaction system to give an optically active alcohol at a high optical purity.

The invention claimed is:

1. A process for producing an optically active alcohol by reacting a ketone substrate in one or more solvent(s) with a hydrogen source in the presence of an asymmetric catalyst, wherein the asymmetric catalyst is metal complex represented by the following general formula (1):

[Chem.1]

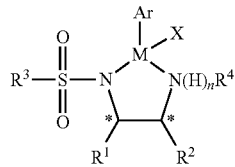

wherein,
$R^1$ and $R^2$ may be identical or different to each other, and is a hydrogen atom, an alkyl group, a phenyl group which may have one or more substituents, a naphthyl group which may have one or more substituents or a cycloalkyl group which may have one or more substituents, or $R^1$ and $R^2$ are bound together to form an alicyclic ring which is unsubstituted or have one or more substituents, $R^3$ is an alkyl group, a perfluoroalkyl group, a naphthyl group which may have one or more substituents, a benzyl group which may have one or more substituents, a phenyl group which may have one or more substituents or a camphor group which may have one or more substituents, $R^4$ is a hydrogen atom or an alkyl group,
Ar is a benzene which may have one or more substituents or a cyclopentadienyl group which may have one or more substituents,
X is an anionic group,
M is ruthenium, rhodium or iridium,
n denotes 0 or 1, where X is not present when n=0
* denotes an asymmetric carbon;
wherein the hydrogen source is a formate salt;
wherein the one or more solvent(s), which is/are capable of dissolving the asymmetric catalyst and the formate salt, comprise(s):
(1) one or more organic solvent(s) except polyethylene glycol,
(2) one or more organic solvent(s) except polyethylene glycol, and one or more water-miscible aprotic solvent(s),
(3) one or more organic solvent(s) except polyethylene glycol, and water,
(4) one or more organic solvent(s) except polyethylene glycol, one or more water-miscible aprotic solvent(s), and water, or
(5) one or more water-miscible aprotic solvent(s), and water; and
wherein the reaction is performed in a homogenous phase.

2. The process for producing an optically active alcohol according to claim 1, wherein the one or more organic solvent(s) is/are a protic solvent(s).

3. The process for producing an optically active alcohol according to claim 1, wherein the one or more organic solvent(s) is/are alcohols having 1 to 5 carbon atoms.

4. The process for producing an optically active alcohol according to claim 1, wherein the one or more organic solvent(s) is/are methanol and/or ethanol.

5. The process for producing an optically active alcohol according to claim 1, wherein the water-miscible aprotic solvent(s) is/are dimethylformamide and/or dimethylsulfoxide.

6. The process for producing an optically active alcohol according to claim 1, wherein the solvents comprise the one or more organic solvent(s) except polyethyleneglycol, and water.

7. The process for producing an optically active alcohol according to claim 1, wherein the solvents comprise the one or more organic solvent(s) except polyethyleneglycol, and one or more water-miscible aprotic solvent(s).

8. The process for producing an optically active alcohol according to claim 1, wherein the solvent(s) comprise water and the one or more water-miscible aprotic solvent(s).

9. The process for producing an optically active alcohol according to claim 1, wherein the solvents comprise the one or more organic solvent(s), one or more water-miscible aprotic solvent(s) and water.

10. The process for producing an optically active alcohol according to claim 1, wherein the formate salt is potassium formate and/or sodium formate.

11. The process for producing an optically active alcohol according to claim 1, wherein the ketone substrate is a cyclic ketone, a ketone having an olefin moiety, a ketone having an acetylene moiety, a ketone having a hydroxyl group, a ketone having a halogen atom, a diketone, a ketoester or a ketoamide.

* * * * *